US009102108B2

(12) United States Patent
Tucker et al.

(10) Patent No.: US 9,102,108 B2
(45) Date of Patent: Aug. 11, 2015

(54) AUTOMATED INSPECTION OF COLORED CONTACT LENSES

(75) Inventors: Robert Carey Tucker, Suwanee, GA (US); Michael Hugh Quinn, Suwanee, GA (US)

(73) Assignee: Novartis AG, Basel (CH)

( * ) Notice: Subject to any disclaimer, the term of this patent is extended or adjusted under 35 U.S.C. 154(b) by 2311 days.

(21) Appl. No.: 11/415,938

(22) Filed: May 3, 2006

(65) Prior Publication Data

US 2006/0251316 A1  Nov. 9, 2006

Related U.S. Application Data

(60) Provisional application No. 60/677,721, filed on May 4, 2005.

(51) Int. Cl.
*B29D 11/00* (2006.01)
*G01N 21/958* (2006.01)

(52) U.S. Cl.
CPC .... *B29D 11/00125* (2013.01); *B29D 11/00317* (2013.01); *G01N 21/958* (2013.01)

(58) Field of Classification Search
USPC ............ 264/1.1, 1.7, 2.5, 40.1; 382/141, 143, 382/152
IPC ......... B29D 11/00125, 11/00317; G01N 21/958
See application file for complete search history.

(56) References Cited

U.S. PATENT DOCUMENTS

| | | | |
|---|---|---|---|
| 3,841,760 A | 10/1974 | Guyton | 356/124 |
| 4,118,730 A | 10/1978 | Lemelson | 358/93 |
| 4,148,061 A | 4/1979 | Lemelson | 358/101 |
| 4,338,626 A | 7/1982 | Lemelson | 358/93 |
| 4,408,291 A | 10/1983 | Gunzberg | 364/900 |
| 4,495,313 A | 1/1985 | Larsen | 523/106 |
| 4,511,918 A | 4/1985 | Lemelson | 358/107 |
| 4,565,348 A | 1/1986 | Larsen | 249/122 |
| 4,640,489 A | 2/1987 | Larsen | 249/122 |
| 4,680,336 A | 7/1987 | Larsen | 524/548 |
| 4,691,820 A | 9/1987 | Martinez | 206/205 |
| 4,889,664 A | 12/1989 | Kindt-Larsen | 264/2.6 |
| 4,956,783 A | 9/1990 | Teranishi | 364/468 |
| 4,969,038 A | 11/1990 | Lemelson | 358/107 |
| 4,979,029 A | 12/1990 | Lemelson | 358/93 |
| 4,980,993 A | 1/1991 | Umezaki | 51/165.71 |
| 4,984,073 A | 1/1991 | Lemelson | 358/93 |
| 5,023,714 A | 6/1991 | Lemelson | 358/107 |
| 5,034,166 A | 7/1991 | Rawlings et al. | 264/1.7 |
| 5,039,459 A | 8/1991 | Kindt-Larsen | 264/2.6 |
| 5,067,012 A | 11/1991 | Lemelson | 358/93 |
| 5,080,839 A | 1/1992 | Kindt-Larsen | 264/2.6 |
| 5,094,609 A | 3/1992 | Kindt-Larsen | 425/445 |
| 5,119,190 A | 6/1992 | Lemelson | 358/93 |
| 5,119,205 A | 6/1992 | Lemelson | 358/93 |
| 5,128,753 A | 7/1992 | Lemelson | 358/101 |
| 5,134,574 A | 7/1992 | Beaverstock | 364/551.01 |
| 5,144,421 A | 9/1992 | Lemelson | 358/101 |
| 5,153,444 A | 10/1992 | Maeda | 250/562 |
| 5,249,045 A | 9/1993 | Lemelson | 358/93 |
| 5,255,331 A | 10/1993 | Kelly | 382/50 |
| 5,283,641 A | 2/1994 | Lemelson | 348/92 |
| 5,303,023 A | 4/1994 | Portney | 356/124.5 |
| 5,339,257 A | 8/1994 | Layden | 364/552 |
| 5,351,078 A | 9/1994 | Lemelson | 348/135 |
| 5,416,570 A | 5/1995 | Kondou | 355/321 |
| 5,443,152 A | 8/1995 | Davis | 206/5.1 |
| 5,461,570 A | 10/1995 | Wang | |
| 5,542,168 A | 8/1996 | Best | 29/407.04 |
| 5,574,554 A | 11/1996 | Su | 356/124 |
| 5,604,583 A | 2/1997 | Byron | 356/124 |
| 5,882,698 A | 3/1999 | Su | 425/215 |
| 6,047,082 A | 4/2000 | Rhody | 382/141 |
| 6,071,112 A | 6/2000 | Calvin | |
| 6,471,891 B1 | 10/2002 | Cameron | |
| 6,719,929 B2 | 4/2004 | Winterton | |
| 6,765,661 B2 | 7/2004 | Biel | 356/124 |
| 7,330,579 B2 * | 2/2008 | Edwards et al. | 382/141 |
| 2001/0041064 A1 * | 11/2001 | Huebner | 396/3 |
| 2001/0045676 A1 | 11/2001 | Winterton | |
| 2002/0093645 A1 * | 7/2002 | Heacock | 356/138 |
| 2004/0004693 A1 | 1/2004 | Chrusch, Jr. | |
| 2004/0114135 A1 | 6/2004 | Edwards | 356/239.2 |
| 2005/0056954 A1 | 3/2005 | Devlin | 264/1.32 |

FOREIGN PATENT DOCUMENTS

| | | |
|---|---|---|
| DE | 63761 | 8/1892 |
| DE | 3432002 A1 | 3/1986 |
| DE | 3432002 C2 | 3/1986 |
| EP | RS 112535 | 10/2005 |
| GB | 604174 | 6/1948 |
| GB | 604178 | 6/1948 |
| GB | 604179 | 6/1948 |
| GB | 604180 | 6/1948 |
| GB | 605171 | 7/1948 |
| GB | 686585 | 1/1953 |
| GB | 2171812 | 9/1986 |
| JP | 04-65993 | * 3/1992 |
| WO | WO 99/32867 | 12/1998 |
| WO | WO 2004/044545 A2 | 5/2004 |
| WO | WO 2005/054807 A2 | 6/2005 |

OTHER PUBLICATIONS

International Preliminary Report.
Written Opinion of the International Searching Authority.
International Search Report.
European Search Report dated Apr. 28, 2010 for European Application No. 10153446.9.

* cited by examiner

*Primary Examiner* — Mathieu Vargot
(74) *Attorney, Agent, or Firm* — Sheng-Hsin Hu; Jian Zhou

(57) ABSTRACT

The present invention relates to a method for manufacturing colored contact lenses, and in particular to automated inspection of colored images printed either on molds or on contact lenses.

20 Claims, No Drawings

AUTOMATED INSPECTION OF COLORED CONTACT LENSES

This application claims benefit under 35 USC §119 (e) of U.S. Provisional Application No. 60/677,721, filed May 4, 2005, incorporated by reference in its entirety.

The present invention relates to a method for manufacturing colored contact lenses, and in particular to automated inspection of colored images printed either on molds or on contact lenses.

BACKGROUND OF THE INVENTION

For cosmetic purposes, colored contact lenses having one or more colorants dispersed in the lens or printed on the lens are in high demand. In general, there are two types of colored contact lenses. The first are contact lenses which use essentially transparent or semi-transparent enhancement colors that allow the color of the natural iris to show through but combine with that natural color to produce a new appearance. Such tinted lenses are typically used to turn a light eye (e.g., green) to a slightly different hue (e.g., aqua). This class of colored lenses may not be able to change an underlying dark colored, brown iris to blue. The second category is the class of opaque colored lenses having a continuous opaque pattern that fully covers the iris or having an intermittent opaque pattern that does not fully cover the iris. Opaque colored contact lenses can effectively and substantially modify the wearer's eye color. Colored contact lenses enhance the natural beauty of the eye, or provide unique patterns on the iris of the wearer, or provide non cosmetic patterns.

Colored contact lenses can be produced in a high volume manufacturing process involving cast-molding and printing on molded lenses or on molds for cast-molding contact lenses (U.S. Pat. No. 5,034,166 to Rawlings et al., herein incorporated by reference in its entirety). The large number of lenses which can be produced per minute necessitates the use of an automated inspection system to ensure not only the quality of a lens but also the quality of a colored print (or image) applied onto a lens.

In the contact lens manufacturing industry, it is well known that automated inspection of contact lenses offers the opportunity to reduce production costs while increasing product consistency. A number of automated inspection systems and methods have been developed for automatically inspecting non-colored contact lenses. Automated inspection of colored images (e.g., iris patterns, inversion marks, orientation marks, etc.) printed on lenses has been described in U.S. Pat. Nos. 6,047,082 and 6,471,891 (herein incorporated by references in their entireties). Recently, U.S. published patent application No. 2004/0114135 also discloses automated inspection of tinted ophthalmic parts. Each of these techniques for automated inspection of colored contact lenses is effective for reducing production costs and increasing product consistency. However, these techniques require that the center of a lens with a colored print applied thereon must be found in a digital image by algorithms prior to analyzing the quality of the pattern on the lens. The need to find the center of the lens in the digital image can be complicated and demand extensive computation if the digital image has a high resolution and/or three colors (red, green, and blue) captured therein. In addition, finding the center of the lens in the digital image may be complicated by the alternation in the configuration of the lens due to handling between removal from the mold and placement in a container suitable for inspection. Moreover, determination of the center of the lens in the digital image could be difficult if the print is non-symmetrical.

Therefore, there still exists a need for automated inspection of colored contact lenses.

SUMMARY OF THE INVENTION

In one respect, the invention provides a method for automatically inspecting a colored print applied on a mold half. The method of the invention comprises: obtaining a mold half including a molding surface, wherein the molding surface includes a colored print; automatically aligning in a precisely pre-determined manner, by using centering and adjusting means, a camera with the mold half having the colored print on its molding surface; taking a picture with the camera, wherein the picture comprises an image of the mold half having the colored print on its molding surface, wherein the predetermined alignment of the camera with the mold half ensures that the center of the mold half image is located substantially at a predetermined pixel in the picture; analyzing by computation at least a pixel area corresponding to the colored print in the mold half image to determine if the colored print applied onto the mold half has any defects.

In another aspect, the invention provides a method for automatically inspecting a colored print applied on a contact lens which is cast-molded in a mold having a male half and female mold half, each mold half have a molding surface. The method of the invention comprises: (1) curing a lens-forming material in a mold for making a contact lens to form a colored contact lens, wherein the mold comprises a male mold half with a first molding surface and a female mold half having a second molding surface, wherein the male and female mold halves are configured to receive each other such that a mold cavity is formed between the first and second molding surfaces when the mold is closed, wherein at least one of the first and second molding surface has a colored print applied thereon prior to dispensing the lens-forming material in the cavity, wherein at least one of the first and second molding surfaces is optically transparent or translucent, wherein the colored print detaches from the molding surface and becomes integral with the body of the colored contact lens; and (2) prior to opening the mold, automatically inspecting colored print quality, wherein this step includes (a) automatically aligning in a precisely pre-determined manner, by using centering and adjusting means, a camera with the mold with the colored contact lens therein, wherein the camera is facing one of the mold halves having the optically-transparent or translucent molding surface, (b) taking a picture with the camera, wherein the picture comprises an image of the mold with the colored contact lens therein, wherein predetermined alignment of the camera with the mold ensures that the center of the mold image is located substantially at a predetermined pixel in the picture; analyzing at least a pixel area corresponding to the colored print in the mold image to determine if the colored print applied onto the colored contact lens has any defects.

In a further aspect, the invention provides a method for making colored contact lenses. The method of the invention comprises the steps of: (1) providing a mold including a male mold half having a first molding surface and a female mold half having a second molding surface, wherein the male and female mold halves are configured to receive each other such that a mold cavity is formed between the first and second molding surfaces when the mold is closed, wherein at least one of the first and second molding surfaces is optically-transparent or translucent; (2) applying a colored print onto an area of a to-be-printed molding surface which is the first or second molding surface; (3) automatically inspecting quality of the colored print applied on the to-be-printed mold half by (a) taking a first picture, wherein the first picture comprises a first image of the mold half with the colored print applied thereon with a camera, (b) analyzing the first image to determine if there are any defects in the colored print, and (c) rejecting the mold half having defects in the colored print thereon; (4) dispensing a specific amount of a lens-forming material into one of the male and female mold halves after successfully passing automatic inspection of the step (3); (5) mating the male and female mold halves to close the mold; (6) curing the lens-forming material located between the two mold halves, thereby forming a molded colored contact lens, wherein the colored print detaches from the molding surface and becomes integral with the body of the colored contact lens; (7) separating the mold into the male and female mold halves, with the colored contact lens adhered on a lens-adhering mold half which is one of the male and female mold halves; (8) optionally and automatically inspecting the colored contact lens adhering on the lens-adhering mold half, wherein the step (8) includes taking a second picture which comprises a second image of the lens-adhering mold half with the colored contact lens thereon and comparing at least each pixel of a pixel area corresponding to the colored print in the second image with each pixel of the first image to determine if the quality of the colored print is substantially preserved during transferring of the colored print from the to-be-printed molding surface to the colored contact lens; (9) removing the colored contact lens from the lens-adhering mold half; and (10) optionally and automatically inspecting the colored contact lens removed from the lens-adhering mold half, wherein the step (10) includes taking a third picture which comprises a third image of the colored contact lens removed from the lens-adhering mold half and comparing at least each pixel of a pixel area corresponding to the colored print in the third image with each pixel of the first image and/or the second image to determine if the colored print applied onto the colored contact lens has any defects, provided that the method comprises at least one of the steps (8) and (10).

In a still further aspect, the invention provides a method for making colored contact lenses. The method of the invention comprises the steps of: (1) providing a mold including a male mold half having a first molding surface and a female mold half having a second molding surface, wherein the male and female mold halves are configured to receive each other such that a mold cavity is formed between the first and second molding surfaces when the mold is closed, wherein at least one of the first and second molding surfaces is optically-transparent or translucent; (2) applying a colored print onto an area of a to-be-printed molding surface which is the first or second molding surface; (3) dispensing a specific amount of a lens-forming material into one of the male and female mold halves; (4) mating the male and female mold halves to close the mold; (5) optionally and automatically inspect quality of the colored print, wherein the inspection is carried out by (a) taking a first picture, wherein the first picture comprises a first image of the mold with the colored print and with the lens-forming material therein with a camera, (b) analyzing the first image to determine if there are any defects in the colored print; (6) curing the lens-forming material located between the two mold halves, thereby forming a molded colored contact lens, wherein the colored print detaches from the molding surface and becomes integral with the body of the colored contact lens; (7) optionally prior to opening the mold, automatically inspect quality of the colored print, wherein the inspection is carried out by (d) taking a second picture, wherein the second picture comprises a second image of the mold with the colored contact lens therein, (b) analyzing the second image to determine if there are any defects in the colored print, and (c) rejecting the mold containing the colored contact lens having defects in the colored print; (8) separating the mold into the male and female mold halves, with the colored contact lens adhered on a lens-adhering mold half which is one of the male and female mold halves; (9) optionally and automatically inspecting the colored contact lens adhering on the lens-adhering mold half, wherein the step (9) includes taking a third picture comprising a third image of the lens-adhering mold half with the colored contact lens thereon and comparing at least each pixel of a pixel area corresponding to the colored print in the third image with each pixel of the first or second image or both to determine if the quality of the colored print is substantially preserved during transferring of the colored print from the to-be-printed molding surface to the colored contact lens; (10) removing the colored contact lens from the lens-adhering mold half; and (11) optionally and automatically inspecting the colored contact lens from the lens-adhering mold half, wherein the step (11) includes taking a fourth picture comprising a fourth image of the colored contact lens removed from the lens-adhering mold half and comparing at least each pixel of a pixel area corresponding to the colored print in the fourth image with each pixel of the first, second, or third image or a combination thereof to determine if the colored print applied onto the colored contact lens has any defects, provided that the method comprises at least one of the steps (9) and (11) and at least one of the steps (5) and (7).

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

A "contact lens" refers to an object that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A contact lens can be tinted before printing any color patterns. A contact lens can be in a dry state or a wet state. "Dry State" refers to a soft lens in a state prior to hydration or the state of a hard lens under storage or use conditions. "Wet State" refers to a soft lens in a hydrated state.

The "front or anterior surface" of a contact lens, as used herein, refers to the surface of the lens that faces away from the eye during wear. The anterior surface, which is typically substantially convex, may also be referred to as the front curve of the lens.

The "rear or posterior surface" of a contact lens, as used herein, refers to the surface of the lens that faces towards the eye during wear. The rear surface, which is typically substantially concave, may also be referred to as the base curve of the lens.

A "colored contact lens" refers to a contact lens (hard or soft) having a colored print applied thereon. A colored print can be any colored image which can be one or more cosmetic patterns, for example, iris-like patterns, Wild Eye™ patterns, made-to-order (MTO) patterns, and the like; an inversion mark that allows a user to handle and insert easily a contact lens; a toric rotation mark, or contact lenses stock keeping units (SKUs), for example, either in forms of numbers or as bar codes. A colored print can be a single color image or a multi-color image.

The term "eye color" refers to the color of the iris.

The term "non-opaque" as used herein is intended to describe transparent or translucent color or a part of the lens that is colored with transparent or translucent coloring.

A "colorant" means either one or more dyes or one or more pigments or a mixture thereof that is used to print a pattern of colored elements on a contact lens.

"Dye" means a substance that is soluble in a solvent and that is used to impart color. Dyes are typically transparent or translucent and absorb but do not scatter light. Dyes can cover both optical regions of contact lenses and non-optical regions of contact lenses.

A "pigment" means a powdered substance that is suspended in a liquid in which it is insoluble. Pigments are used to impart color. Pigments, in general, are more opaque than dyes.

The term "a conventional or non-pearlescent pigment" as used herein is intended to describe any absorption pigments that impart color based on the optical principle of diffuse scattering and its color is independent of its geometry.

"Pearlescence" means having a pearly luster; resembling a pearl in physical appearance; or having a nearly neutral slightly bluish medium gray color.

A "pearlescent pigment" refers to a class of interference (effect) pigments, which are transparent thin platelets of low refractive index material (e.g., transparent mica platelets) coated with optically thin coating of a high refractive index material (e.g., metal oxide, such as, for example titanium oxide or iron oxide), and which impart color mainly based on the optical principle of thin-film interference. This class of pigment can provide pearly luster and iridescent effects.

A "lens-forming material" refers to a polymerizable composition which can be can be (cured (i.e., polymerized and/or crosslinked) thermally or actinically (i.e., by actinic radiation) to obtain a crosslinked polymer. Examples of actinic radiation are UV irradiation, ionized radiation (e.g. gamma ray or X-ray irradiation), microwave irradiation, and the like. Thermal curing or actinic curing methods are well-known to a person skilled in the art. Lens-forming materials are well known to a person skilled in the art. Any known suitable lens-forming materials can be used in the invention. Examples of lens-forming materials include lens formulations for making non-silicone hydrogel contact lenses and silicone hydrogel contact lenses.

"Hydrogel" means a polymeric material which has having an equilibrium content between about 10 and 90 percent water.

A "HEMA-based hydrogel" refers to a hydrogel obtained by copolymerization of a polymerizable composition comprising hydroxyethylmethacrylate (HEMA).

A "silicone hydrogel" refers to a hydrogel obtained by copolymerization of a polymerizable composition comprising at least one silicone-containing monomer or at least one silicone-containing macromer.

"Hydrophilic," as used herein, describes a material or portion thereof that will more readily associate with water than with lipids.

A "prepolymer" refers to a starting polymer which can be cured (e.g., crosslinked and/or polymerized) actinically or thermally or chemically to obtain a crosslinked and/or polymerized polymer having a molecular weight much higher than the starting polymer. A "crosslinkable prepolymer" refers to a starting polymer which can be crosslinked upon actinic radiation to obtain a crosslinked polymer having a molecular weight much higher than the starting polymer.

A "monomer" means a low molecular weight compound that can be polymerized. Low molecular weight typically means average molecular weights less than 700 Daltons.

A "vinylic monomer", as used herein, refers to a low molecular weight compound that has an ethylenically unsaturated group and can be polymerized actinically or thermally. Low molecular weight typically means average molecular weights less than 700 Daltons.

The term "ethylenically unsaturated group" or "olefinically unsaturated group" is employed herein in a broad sense and is intended to encompass any groups containing at least one >C=C< group. Exemplary ethylenically unsaturated groups include without limitation acryloyl, methacryloyl, allyl, vinyl, styrenyl, or other C=C containing groups.

A "macromer" refers to a medium and high molecular weight compound or polymer that contains functional groups capable of undergoing further polymerizing/crosslinking reactions. Medium and high molecular weight typically means average molecular weights greater than 700 Daltons. Preferably, a macromer contains ethylenically unsaturated groups and can be polymerized actinically or thermally.

A "polymer" means a material formed by polymerizing/crosslinking one or more monomers.

An "interpenetrating polymer network (IPN)" as used herein refers broadly to an intimate network of two or more polymers at least one of which is either synthesized and/or crosslinked in the presence of the other(s). Techniques for preparing IPN are known to one skilled in the art. For a general procedure, see U.S. Pat. Nos. 4,536,554, 4,983,702, 5,087,392, and 5,656,210, the contents of which are all incorporated herein by reference. The polymerization is generally carried out at temperatures ranging from about room temperature to about 145° C.

A "print-on-mold process for producing colored contact lenses" refers to a process for molding a colored contact lens described in U.S. Pat. No. 5,034,166 to Rawlings et al. (herein incorporated by reference in its entirety).

A "spatial limitation of actinic radiation" refers to an act or process in which energy radiation in the form of rays is directed by means of, for example, a mask or screen or combinations thereof, to impinge, in a spatially restricted manner, onto an area having a well defined peripheral boundary. For example, a spatial limitation of UV radiation can be achieved by using a mask or screen which has a transparent or open region (unmasked region) surrounded by a UV impermeable region (masked region), as schematically illustrated in FIGS. 1-9 of U.S. Pat. No. 6,627,124 (herein incorporated by reference in its entirety). The unmasked region has a well defined peripheral boundary with the masked region.

The term "align in a precisely pre-determined manner" or "predetermined alignment", in reference to a camera, a mold, or a mold half, is intended to describe an alignment process in which the camera and the mold or the mold half is physically aligned by physical means in a way so that, in a picture taken by the camera and comprising an image of the mold or mold half, the center of the mold or mold half image is located substantially at a predetermined pixel in the picture. In accordance with the invention, the predetermined pixel can be anywhere in the picture, but preferably is within a radial distance of about 20 pixels or less, preferably of about 10 pixels or less, more preferably about 5 pixels or less, even more preferably about 2 pixels or less from the central pixel (i.e., the center of the picture). Most preferably, the center of mold or mold half image is located at the central pixel (i.e., the center of the picture). The term "precisely" is intended to describe that the location of the center of the mold or mold half image can be known at a position of a picture with a precision of 2.0 mm or less, preferably 1.0 mm or less, more preferably 0.5 mm or less (in the picture).

A "solid color disk" refers to a substantially circular colored pattern which is substantially free of voids (non-printed areas).

As well known in the art, a color is generally described mainly by the following inter-related terms: hue, chroma, intensity, saturation, luminance, brightness value and opacity. The term "different colors" is intended to describe that two colors are different in at least one of hue, chroma, intensity, saturation, luminance, brightness value, and opacity.

The term "lightly tinted" is intended to describe that a contact lens is tinted with a tinting agent in an edge-to-edge manner or at least in the central zone of a lens. A person skilled in the art will understood how to tint a lens, for example, by incorporating a tinting agent (a dye or a pigment) in a lens-forming material for making contact lenses.

In general, the invention is directed to improved and efficient methods for automatic inspection of one or more colored prints applied onto a mold for making a colored contact lens or a colored contact lens produced according to a print-on-mold process for producing colored contact lenses and also to manufacturing processes of colored contact lenses involving automated inspection of colored prints of the invention.

It is discovered that there is no need for locating, through analysis by algorithms, the center of an image of either a colored print applied on a molding surface of a mold half or a colored print on a cast-molded contact lens, which is still within a mold prior to mold opening or is still adhered on one of mold halves of a mold after mold separation. The center of a mold surface of a mold or mold half is well defined mechanically, the center of a colored contact lens in the mold or on the mold half is known precisely and fixed, and any picture has a predefined central pixel. Likewise, the position of camera placed to view the lens in a mold or on a mold half can also be known exactly. Now, it is a matter of coordinating the movement of the mold and the camera. By using centering and adjusting means which is associated with each mold or mold half and/or camera, one can accurately align a camera with a mold or a mold half in a precisely determined way so that, in any picture taken by the camera and comprising an image of the mold or mold half, location of the center of the mold or mold half image is predetermined and well known in the picture. For example, the center of the mold or mold half image is located at the central pixel of the picture (i.e., the center of the picture). Furthermore, for any mold having at least one optically-transparent molding surface, a colored print on a mold can be inspected through the optically-transparent molding surface. Without a step of finding the center of a colored lens in a digital image through a complicated and extensive computation based on one or more algorithms, one can therefore enhance the efficiency in automated inspection of a colored print on a mold half or a colored contact lens.

In one respect, the invention provides a method for automatically inspecting a colored print applied on a mold half. The method of the invention comprises: obtaining a mold half including a molding surface, wherein the molding surface includes a colored print; automatically aligning in a precisely pre-determined manner, by using centering and adjusting means, a camera with the mold half having the colored print on its molding surface; taking a picture with the camera, wherein the picture comprises an image of the mold half having the colored print on its molding surface, wherein predetermined alignment of the camera with the mold half ensures that the center of the mold half image is located substantially at a predetermined pixel in the picture; analyzing by computation at least a pixel area corresponding to the colored print in the mold half image to determine if the colored print applied onto the mold half has any defects.

In accordance with the invention, a colored print can be non-opaque or opaque. A colored print can comprise non-opaque patterns that can enhance the color of the natural iris, opaque patterns that effectively and substantially modify the wearer's eye color or provide unique patterns on the iris of the wearer, an inversion mark that allows a user to handle and insert easily a contact lens, a toric rotation mark, or contact lenses stock keeping units (SKUs), or combinations thereof. A colored print can be a single color image or a multi-color image. Examples of colored prints includes without limitation those shown in commercial products, for example, FRESHLOOK® color contact lenses, Focus® SOFT COLORS®, CIBASOFT® SOFTCOLORS®, Wild Eye™. Examples of non-opaque patterns and opaque patterns includes without limitation a transparent or translucent solid color disk, a transparent or translucent annular solid color ring, a color disk with a radial gradient of color intensity in which the color intensity changes from light or transparent to dark in a radial direction from the center to the edge of the central zone as disclosed in a copending and commonly assigned U.S. patent application No. 60/636,930 filed Dec. 17, 2007 (herein incorporated by reference in its entirety), iris patterns disclosed in U.S. Pat. Nos. 4,582,402, 5,414,477, 5,120,121, 4,634,449, 4,954,132, 5,793,466 and European Patent No. 0 472 496 A2 (herein incorporated by references in their entireties).

A colored print can be formed by applying one or more layers of non-opaque and/or opaque patterns onto a molding surface of a mold. A transparent or translucent colorant can be applied to a circular area of the contact lens covering the iris and pupil of the contact lens wearer's eye or to an annular area of the contact lens covering only the iris of the contact lens wearer's eye. An opaque colorant generally is applied to an annular area of the contact lens covering only the iris of the contact lens wearer's eye to form a colored, opaque, intermittent patterns. The pattern leaves a substantial portion of the iris section within the interstices of the pattern non-opaque or lightly tinted. The opaque pattern or patterns can be made up of dots having regular or irregular, uniform or non-uniform shapes, for example, round, square, hexagonal, elongated, or other dot shapes. Further, the elements of the pattern may have a shape other than dots, so long as the elements are indiscernible to the ordinary viewer, cover between 10 and 30 percent, preferably about 20 percent of the iris, and leave a substantial portion of the iris section within the interstices of the pattern non-opaque. The patterns that make up the portions of the iris can be islands of color or worms, corkscrews, starbursts, spokes, spikes, striations, radial stripes, zig-zags and streaks. In certain cases, a single transparent or translucent color background is used to complement the multi-pattern design. These patterns blend with each other to provide a colored contact lens that enhances the structure of the iris of a person wearing the lens.

In a preferred embodiment, an inversion mark and/or other marks (e.g., rotation mark, toric marks (cylindrical axis, ballast axis), SKU, UPC codes, etc.) can be embedded in a colored pattern so that the those marks are noticeable to a wearer before wearing the colored lens whereas unnoticeable to an ordinary viewer when worn by a wearer.

A preferred method for applying an ink including at least one colorant onto a contact lens in accordance with this invention is through printing, such as for example, pad transferring printing and/or inkjet printing using an ink, preferably a water-based ink.

An ink typically comprises at least one colorant, a binder polymer, a solvent, and one or more other components selected from the group consisting of a crosslinker, a humectant, a surfactant, a monomer, a polymerization initiator, an antimicrobial agent, an antioxidant agent, an anti-kogating agent, and other additives, as well known to a person skilled.

Pad transfer printing is well known in the art (see. For example, U.S. Pat. No. 3,536,386 to Spivack; U.S. Pat. Nos. 4,582,402 and 4,704,017 to Knapp; U.S. Pat. No. 5,034,166 to Rawlings et al., herein incorporated by reference in their entireties). A typical example of this printing follows. An image (or patterns) is etched into metal to form a cliché. The cliché is placed in a printer. Once in the printer, the cliché is inked by either an open inkwell doctoring system or by a closed ink cup sliding across the image. Then, a silicone pad picks up the inked image from the cliché and transfers the image to the molding surface of a mold half. The silicone pads are made of a material comprising silicone that can vary in elasticity. The properties of the silicone material permit the inks to stick to the pad temporarily and fully release from the pad when it contacts a contact lens or a mold. Appropriate pad-transfer printing structures include, but are not limited to, Tampo-type printing structures (Tampo vario 90/130), rubber stamps, thimbles, doctor's blade, direct printing, or transfer printing as they are known in the art.

Any known suitable silicone pad can be used in the present invention. Silicone pads are commercially available. However, different pads could give different print qualities. A person skilled in the art will know how to select a pad for a given ink.

Clichés can be made of ceramics or metals (e.g., steel). Where a cliché is made of a steel, it would be desirable to neutralize the pH of a water-based ink (e.g., adjusted pH to 6.8~7.8) by adding a buffer (such as, for example, phosphate salts). Images can be etched into a cliché according to any methods known to a person skilled in the art, for example, by chemical etching or laser ablation or the like. It is also desirable to clean clichés after use using standard cleaning techniques known to a person skilled in the art, such as, for example, immersion in a solvent, sonication, or mechanical abrasion.

Printing the lens using an inkjet printing process is described in published US Patent Application Nos. 2001/0050753, 2001/0085934, 2003/0119943, and 2003/0184710, herein incorporated by references in their entireties.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material. Alternatively, a single sided molding method could be used, where one side is cast molded, and the other side is lathed.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

Any known suitable centering and adjusting means can be used in the invention. Examples of centering and adjusting means include without limitation guiding surface associated with a mold or mold half and with a camera and guiding rods associated with a mold or mold half and with a camera. A person skilled in the art will know well to design centering and adjusting means for precisely aligning a camera with a mold or mold half at a predetermined manner.

A person skilled in the art will know how to calibrate predetermined alignment of a camera with a mold or mold half. For example, one can use a mold half, the center of its molding surface of which is marked clearly with a print (e.g., a cross), as a calibration tool for adjusting centering and adjusting means so that the center of the mold half image is precisely located at a predetermined pixel in a taken picture.

In accordance with the invention, any cameras can be used in the invention so long as they can generate digital pictures composed of pixels. A camera can be a gray-scale or color camera.

Where a camera is a gray-scale camera, in an image captured by the camera, the light intensity of each pixel is assigned a value of, e.g., 0 to 255, and is then registered in a coordinate system, such as Cartesian or polar coordinate system.

In accordance with a preferred embodiment, the light intensity of pixels of the image is registered in polar coordinates. This light intensity information in polar coordinate form is stored in a matrix wherein light intensity values at incremented angles are listed in rows of the matrix and the light intensity values for incremental radii are listed in columns. This matrix presentation of the light intensity data facilitates the analysis of defects. The matrix shall be referred to hereafter as the S-matrix.

Preferably, a 1024 by 1024 pixel array is used to capture the image for the single gray-scale image, although less or more resolution can be used if desired.

Where a color camera is used, a picture (or image) can be divided into the red, green and blue layers on 3 chips in the color camera and three color images (red, green and blue color images) can be created by the camera. The light intensity of pixels in each color image can be registered as described above. For color images, preferably fewer pixels are used, e.g., 768 by 494 pixel arrays for each color image, because more calculations have to be performed when three colors are captured within an individual images.

"Taking a picture" or "capturing an image" can be accomplished according to any known suitable methods. A person skilled in the art will understand well how to select a light source for taking a picture. An Illumination light can be a continuous or pulse light.

Considering that the level of ambient light may cause variations in an image of a print under inspection, it is desirable that the output of a camera is normalized for variations in ambient light across the field of the image. This normalization process ensures that the image of the lens under inspection is not affected by variations in ambient light. Alternately, collimated light could be used to minimize the variations in ambient light.

It is preferably that the illumination is normalized. Uneven illumination can arise because of variations in either the illumination system or in the optical elements of the imaging system. The illumination variations typically have a slow variation across the image. The effect of these variations can be greatly reduced by using a normalization algorithm which is described in U.S. Pat. No. 6,047,082 (herein incorporated by reference in its entirety).

In accordance with the invention, defects in a colored print applied onto a mold half or a contact lens can include, without limitation, imperfections in a printed iris pattern, imperfections in printing a logo, an inversion mark, a toric rotation mark, or stock keeping units (SKUs), the unwanted presence of colorant in a particular area (e.g., the optical zone or the peripheral zone of a colored contact lens). Examples of imperfections in a printed iris pattern includes without limitation decentralization of the printed iris pattern (i.e., being not correctly centered), a variety of misprints (e.g., the absence of colorant in a particular area, a fairly large blank area in an iris pattern, the presence of too much colorant (an excess) in a particular area) which can reduce the attractiveness and functionality of a contact lens. Examples of imperfections in printing a logo, an inversion mark, a toric rotation mark, or stock keeping units (SKUs) include without limitation a damaged or missing print, a misaligned toric rotation mark or inversion mark, and the likes. The presence of any defects in a colored print will allow one to reject the mold half with the colored print applied thereon. Only those mold halves with colored prints applied thereon which pass inspection of the colored prints can be used for production of colored contact lenses.

Typically, a colored contact lens comprising a circular non-opaque pupil section (i.e., optical zone), an annular iris section surrounding the pupil section, and a non-opaque peripheral section surrounding the iris section. When worm, the pupil section allows for a clear pathway of light to the pupil and can have an uneven or substantially even border with the iris section.

Any known suitable algorithms can be used in analyzing by computating at least a pixel area corresponding to the colored print in the mold half image to determine if the colored print applied onto the mold half has any defects. For example, decentralization of an iris print applied onto a mold half can be determined by the radial distances (from the central pixel or a predetermined pixel) of at least three pixels which are closest to the central pixel (or the predetermined pixel) and are not collinear. These pixels would be separated by, for example, at least 45 degrees (in a polar coordinate system referenced to the central pixel or the predetermined pixel). Where the pupil section of a colored contact lens has an even border with the iris section, one can determine if the even border is concentric with the central pixel (or the predetermined pixel). Alternatively, one can use pixels located along the boundary of the iris section with the peripheral section to determine if there is any decentralization of an iris pattern. It is understood that any other algorithms can be used in the invention to determine if there is any decentralization of an iris pattern.

If the decentralization of an iris pattern is above a threshold, e.g., greater than about 1.00 mm, preferably greater than about 0.75 mm, more preferably greater than about 0.50 mm, even more preferably greater than about 0.20 mm, the mold half with the iris print applied thereon is rejected. The above-described decentralization values are actual values in the actual scale of a mold half without any enlargement or reduction.

Where three color images (red, green and blue color images) are created by a camera, one or more algorithms can be used to determine decentralization of each color image based on any processes as described previously.

The pupil section and the peripheral section are inspected to see if there is any stray colorant, especially opaque colorant, present in those areas. Colorant can mistakenly drip, or splash in the pupil section or the peripheral section during printing (e.g., pad printing or inkjet printing), or be present within these sections by the application of a improperly located colorant layer. The pupil section (optical zone) is a circular zone having a diameter of from about 3 mm to about 5 mm. For analysis, values for the sensitivity threshold, which is an allowable contrast in light intensity between neighboring pixels, minimum defect size, which is an area in which the light intensity values of the pixels are not within an acceptable range of intensities, and the defect size thresholds, which is the minimum allowable sum of the area of all the defects in a zone, are inputted into an algorithm and used by the system during the area inspections. As known to a person skilled in the art, each section can have different sensitivities and defect sizes depending upon how important it is to have an area free of excess colorant, or other defects in the colorant.

Generally, the sensitivity of the pupil section (optical zone) is high and the allowable amount of excess colorant is very low, since excess colorant can adversely affect visual acuity. In contrast, the sensitivity of the iris section can be relatively lower to allow some excess colorant. Excess colorant is a cosmetic consideration in the iris section and does not effect visual acuity. Similarly, the peripheral section surrounding the iris section may also have lower sensitivity and a higher allowable area of excess ink than the pupil section. All of these sensitivity values can be determined by analyzing acceptable and unacceptable colored lenses made from the molds with colored prints applied thereon.

In accordance with the invention, a colored print can be analyzed for clear spots (i.e., substantially free of colorant) of excessive size. Preferably, algorithms described in U.S. Pat. No. 6,047,082 (herein incorporated by reference in its entirety) is used to analyze a colored print for clear spots (i.e., substantially free of colorant) of excessive size. It is understood that the clear spots can also be lightly tinted or has a single transparent or translucent color background.

The colored print can be inspected with a set of data that can easily be gathered since the center of the mold half (or lens) and the colored print has been known, for example, precisely at the central pixel (or any predetermined pixel) of the picture. This data set is an array of image brightness values along radial lines at regular angle intervals around the compass of the mold half (or lens). The brightness values along each radial line are stored in the S-matrix. As explained previously, the S-matrix columns contain the values along a path of constant angle and the rows contain the values along a path of constant radius. The iris portion of the S-matrix represents a picture of the brightness values within a region bounded by an inner radius ($r_1$) and an outer radius ($r_2$) of the iris print zone and a first angle ($\theta_1$) and a second angle ($\theta_2$), but displayed on a rectangular row and column format. In analysis, the angles $\theta_1$ and $\theta_2$ are selected to cover the entire circle from 0 to 360 degrees.

This description of the S-matrix assumes that the radial paths cross a circular path centered on the mold half (or lens) center. A more sophisticated version of the algorithm can use an elliptical or polynomial generated path that models the shape of the mold half (or lens).

The size of the S-matrix is M×N, where M is the number of points taken along a path of constant angle and N is the number of angles. Experimentation can be done with the best size for S. The trade-off is between more detail and more processing time. Since the purpose is to find fairly large blank areas in the colored pattern, it is not necessary to use a large number of points in S. The best size to use can be determined empirically.

It is understood that an iris color pattern can have a number of medium size gaps in the printed area, but this is a part of the pattern design. Such ink pattern is acceptable. In contrast, a large unprinted region running through the printed area should clearly be a defect and be rejected.

The contrast between the bright areas and the colored pattern can be enhanced by a standard contrast enhancement procedure. This procedure consists of applying a point function u=f(s) to each element "s" of the array in such a way that the gray levels are spread more evenly over the total range of brightness values. However, this process takes time, with at least one multiplication per element of the S-matrix, and does not accomplish anything useful toward the goal of detecting bright areas. Such a process is useful to match the image of S with a detector such as the human visual system, but is not useful in an automated detection process where one can tailor the detector to the image. Instead, we use a process of threshold detection as described below.

Threshold detection can be used to differentiate pixels that have bright values from others that do not. Let a threshold (T) function be defined by u=f(s), where $$f(s) = \begin{cases} 1, & s \geq T \\ 0, & s < T \end{cases}$$

As a matter of implementation, the U-matrix is scaled so that 0 is the minimum (black) and 1 is the maximum (white). Applying the threshold function to S will produce a new array, say U, in which all of the values are either 0 or 1. A region of S that has a large number of bright areas will appear in U as a cluster of ones.

The choice of the threshold is important, but not particularly sensitive. It should be between the highest gray level of a printed pixel and the brightness value of an unprinted pixel. There is a range of values that can be used for the threshold (T). The value of T can be set automatically in an operational system by measuring the average brightness over the optical zone for several lenses in sequence. If you set the threshold just on the current lens, then a cloudy optical zone may lead to a value that is too low for T. T should be set to be about 20 brightness steps lower than the average. As an example, the average brightness in the center zone of the lens could be 242, which would place a threshold at 222. Using this automated technique will ensure that the printing will be lower than T and will appear black in the U-matrix. Automatic setting of T is recommended for robust operation.

The range of possible threshold values can be verified by examining the brightness histogram.

One can conduct a search for bright areas by summing over a rectangular region that is stepped over the array U. One would expect the sum to be large in bright areas and small in other areas. The size of the block should be approximately the size of the smallest bright area in a printed zone that would lead to a rejection. The step size is a trade-off between efficiency and the need to be sure that the window steps within the bright area.

Let A be a matrix in which A(i,j) is the sum of the values of U within the block located at position (i,j). Then A will have a large value when the block is over a bright area and a small value when it is over a dark area. A surface plot of A for a block size of 50×50 and a step size of 10 in each direction has a peak at column 21 and row 6.

To look for larger problems in the print area it is necessary to increase the size of the inspection box, for example, an inspection box of size 100×100 fits within an unprinted area. This provides an indication of the size to be chosen for the inspection box.

The analysis program has the following components:

1. Select the rows of the S-matrix that correspond to the printed area. The selected rows should cover the printed area but not pick up the bright area in the optical zone and outside the printed area.

2. Construct a matrix U that is a thresholded version of S. The threshold should be about 20 brightness steps below the average brightness in the optical zone.

3. Scan the U-matrix with an inspection box that is about the same size as the gaps in the printed zone that you want to detect.

4. Reject the mold half or lens if any of the boxes have a sum that is greater than an acceptable threshold. This threshold should be about 80% of the size of the scanning box.

Inspection of a logo, an inversion mark, a toric rotation mark, or stock keeping units (SKUs) can be preferably carried out according to the procedure described in U.S. Pat. No. 6,047,082, herein incorporated by reference in its entirety. Those marks can be used in analysis for easy recognition of the rotational position and displacement of each colorant layer. Commercially available pattern recognition software could be adapted to locate those marks and to measure the angle and displacement between each of the marks. This technique would then provide a means to compare the relative position of the different colorant layers that does not rely on finding the center of an individual colorant layer.

Where a single transparent or translucent color background is used to complement the multi-pattern design, the inspection could be performed by an algorithm that would determine based on the relative intensity values. For example, the lowest intensity value would correspond to no color, the next level of intensity values would correspond to the first colorant, e.g. transparent or translucent color background, and the next range of intensity values would correspond to the second colorant, e.g. a layer of opaque colorant. The values assigned to each colorant can also be checked by knowing the pattern for each colorant and comparing the pixel intensity values in the captured image to the expected location of the pixels in the colored print.

In a preferred embodiment, the image of the colored print applied onto a mold half can be compared with a designed image of the colored print stored in a computer as well known to a person skilled in the art. The light intensities and positions in relation to the picture center of pixels in an image of the colored print and in the designed image of the colored print can be compared as a whole, by analyzing all portions of each image in a systematic manner. More preferably, the images can be compared in discrete zones.

In accordance with the invention, when two or more images are compared with each other, they should be in the same scale in size.

In a more preferred embodiment, a colored print (or rotational orientation of a colored print in reference to its center) applied onto a mold half, the image of the colored print on the mold half, and a designed image of the colored print stored in a computer all are aligned at a predetermined angular orientation (with their corresponding centers are predetermined and known). Predetermined angular orientation of a colored print (or rotational orientation of a colored print in reference to its center) applied onto a mold half can be achieved by properly aligning a cliche and/or the mold half. Predetermined angular orientation of the image of the colored print on the mold half can be achieved by physically means in the step of automatically aligning a camera with the mold or mold half.

With such predetermined angular orientation, it is more easily to compare the two images to check any print defects and/or determine the rotation of the colorant layers. Rotation of a colorant layer's pattern can be determined relative to its designed image. This is accomplished by comparing the angular position of one or more features in the pattern. The angle between a feature on the outer edge of the designed image and the corresponding feature on the captured image yields the amount of rotation. The algorithm can provide for multiple features or for the ability to repeat the search if an attempt to find a feature is unsuccessful, such as in the case of distortion of the applied colorant or a missing area of pattern on the captured image. The amount of rotation of the pattern is the angular difference between the expected or desired position of the feature in the designed image and the location of the feature in the captured image and can be averaged if multiple individual angle measurements are measured. Where multiple colorant layers must be applied in exact angular positions to achieve a desired cosmetic effect, the rotation of each pattern may be very important.

In another aspect, the invention provides a method for automatically inspecting a colored print applied on a contact lens which is cast-molded in a mold having a male half and female mold half, each mold half have a molding surface. The method of the invention comprises: (1) curing a lens-forming material in a mold for making a contact lens to form a colored contact lens, wherein the mold comprises a male mold half with a first molding surface and a female mold half having a second molding surface, wherein the male and female mold halves are configured to receive each other such that a mold cavity is formed between the first and second molding surfaces when the mold is closed, wherein at least one of the first and second molding surface has a colored print applied thereon prior to dispensing the lens-forming material in the cavity, wherein at least one of the first and second molding surfaces is optically transparent or translucent, wherein the colored print detaches from the molding surface and becomes integral with the body of the colored contact lens; and (2) prior to opening the mold, automatically inspecting colored print quality, wherein this step includes (a) automatically aligning in a precisely pre-determined manner, by using centering and adjusting means, a camera with the mold with the colored contact lens therein, wherein the camera is facing one of the mold halves having the optically-transparent or translucent molding surface, (b) taking a picture with the camera, wherein the picture comprises an image of the mold with the colored contact lens therein, wherein predetermined alignment of the camera with the mold ensures that the center of the mold image is located substantially at a predetermined pixel in the picture, (c) analyzing at least a pixel area corresponding to the colored print in the mold image to determine if the colored print applied onto the colored contact lens has any defects.

A colored print can be applied on the molding surface defining the posterior (concave) surface of a contact lens or on the molding surface defining the anterior surface of a contact lens or on both mold portions. Preferably, a colored print is applied on the molding surface defining the anterior surface of a contact lens.

Optionally, a transferable coating can be applied to a molding surface of a mold before applying the ink by pad transfer printing or inkjet printing. A transferable coating is intended to describe a coating which can be detached from a molding surface of a mold and become integral with the body of a contact lens molded in the mold. A transferable coating can be applied to a molding surface of mold by any suitable techniques, such as, for example, spraying, printing, swabbing, or dipping. A transferable coating can be prepared from a solution comprising polymerizable components and free of any colorants. For example, a transferable coating with substantially uniform thickness (less than 200 microns) can be prepared by spraying a molding surface with a solution having the composition (without colorant) of an ink to be used or a solution of prepolymer or a lens-forming material to be used. This transferable coating can optionally be dried or cured to form a transferable clear film (without any pigment but optionally with dyes including reactive dyes). One or more colored patterns can then be printed on this transferable coating or film. By applying a transferable coating before printing, one can make a colored lens in which printed colored patterns are imbedded just below a film derived from the transferable coating. Such lens may be more comfortable for wearing and have much less susceptibility to colorant leaching out of the colored lens.

After printing an ink of the invention on a molding surface of a mold, the printed ink can be partially or completely cured by UV, other actinic radiation, or thermal means to form a colored film in accordance with the invention. It is desirable that the printed ink is cured actinically to an extent to minimize loss of pattern definition resulted from subsequent filling of a lens-forming material.

Any lens-forming materials can be used in the invention and is not presently considered a critical part of this aspect of the invention. Lens forming materials that are suitable in the fabrication of contact lenses are illustrated by numerous issued US patents and familiar to those skilled in the art. Preferred lens-forming materials are capable of forming hydrogels. A lens-forming material can comprise one or more prepolymers, optionally one or more vinylic monomers and/or macromers and optionally further include various components, such as photoinitiator, visibility tinting agent, fillers, and the like. It should be understood that any silicone-containing prepolymers or any silicone-free prepolymers can be used in the present invention.

A preferred group of lens-forming materials are prepolymers which are water-soluble and/or meltable as described above. It would be advantageous that a lens-forming material comprises primarily one or more prepolymers which are preferably in a substantially pure form (e.g., purified by ultrafiltration). Therefore, after crosslinking/polymerizing by actinic radiation, a contact lens may require practically no more subsequent purification, such as complicated extraction of unpolymerized constituents. Furthermore, crosslinking/polymerizing may take place solvent-free or in aqueous solution, so that a subsequent solvent exchange or the hydration step is not necessary.

A person skilled in the art will known well how to actinically or thermally cure the lens-forming material within the lens-forming cavity to form the contact lens.

In a preferred embodiment, where a lens-forming material is a solution, solvent-free liquid, or melt of one or more prepolymers optionally in presence of other components, reusable molds are used and the lens-forming material is cured actinically under a spatial limitation of actinic radiation to form a colored contact lens. Examples of preferred reusable molds are those disclosed in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties.

In this case, the lens-forming material is put into a mold consisting of two mold halves, the two mold halves not touching each other but having a thin gap of annular design arranged between them. The gap is connected to the mold cavity, so that excess lens material can flow away into the gap. Instead of polypropylene molds that can be used only once, it is possible for reusable quartz, glass, sapphire molds to be used, since, following the production of a lens, these molds can be cleaned and dried rapidly to effectively remove the uncrosslinked prepolymer and other residues, using water or a suitable solvent. Reusable molds can also be made of Topas® COC grade 8007-S10 (clear amorphous copolymer of ethylene and norbornene) from Ticona GmbH of Frankfurt, Germany and Summit, N.J. Since the mold halves do not touch each other in the region of the lens to be produced, i.e. the cavity or actual mold faces, damage as a result of contact is ruled out. This ensures a high service life of the molds, which, in particular, also ensures high reproducibility of the contact lenses to be produced.

The two opposite surfaces (anterior surface and posterior surface) of a contact lens are defined by the two molding surfaces while the edge is defined by the spatial limitation of actinic irradiation rather than by means of mold walls. Typically, only the lens-forming material within a region bound by the two molding surfaces and the projection of the well defined peripheral boundary of the spatial limitation is crosslinked whereas any lens-forming material outside of and immediately around the peripheral boundary of the spatial limitation is not crosslinked, and thereby the edge of the contact lens should be smooth and precise duplication of the dimension and geometry of the spatial limitation of actinic radiation. Such method of making contact lenses are described in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627, 124, which are incorporated by reference in their entireties.

A spatial limitation of actinic radiation (or the spatial restriction of energy impingement) can be effected by masking for a mold that is at least partially impermeable to the particular form of energy used, as illustrated in U.S. patent application Ser. No. 08/274,942 filed Jul. 14, 1994 and U.S. Pat. No. 6,627,124 (herein incorporated by reference in their entireties) or by a mold that is highly permeable, at least at one side, to the energy form causing the crosslinking and that has mold parts being impermeable or of poor permeability to the energy, as illustrated in U.S. patent application Ser. No. 10/732,566 filed Dec. 10, 2003, Ser. No. 10/721,913 filed Nov. 25, 2003 and U.S. Pat. No. 6,627,124 (herein incorporated by reference in their entireties). The energy used for the crosslinking is radiation energy, especially UV radiation, visible light radiation, gamma radiation, electron radiation or thermal radiation, the radiation energy preferably being in the form of a substantially parallel beam in order on the one hand to achieve good restriction and on the other hand efficient use of the energy.

Previously-described various embodiments of colored prints, printing methods, inks, lens molds, centering and adjusting means, cameras, taking pictures (or capturing images), and analysis of images for defects can be incorporated in this aspect of the invention.

Any lenses having one or more print defects will be rejected. The presence of any defects in a colored print will allow one to reject the resultant colored lens or the mold with the colored lens therein if the mold is a disposable mold. Only those molds with colored lens therein which pass inspection of the colored prints will be subjected to further processes, such as, for example, demolding, extraction, hydration, surface treatment, sterilization (e.g., autoclave), or combinations thereof.

In a preferred embodiment, the image of the colored print, which detaches from the molding surface and becomes integral with the body of the colored contact lens, can be compared with a designed image of the colored print stored in a computer as well known to a person skilled in the art. The light intensities and positions in relation to the picture center of pixels in an image of the colored print and in the designed image of the colored print can be compared as a whole, by analyzing all portions of each image in a systematic manner. More preferably, the images can be compared in discrete zones. Even more preferably, a colored print applied onto a mold half, a designed image of the colored print stored in a computer, and the image of the mold with the colored contact lens therein all are aligned at a predetermined angular orientation (with their corresponding centers are predetermined and known).

In another preferred embodiment, the method of the invention further comprises a step of automatically inspecting quality of the colored print applied onto at least one of the first and second molding surface prior to dispensing the lens-forming material in the cavity. This step is carried out by: automatically aligning in a precisely pre-determined manner, by using centering and adjusting means, a camera with the mold half having the colored print on its molding surface; taking a picture with the camera, wherein the picture comprises an image of the mold half having the colored print on its molding surface, wherein predetermined alignment of the camera with the mold half ensures that the center of the mold half image is located substantially at a predetermined pixel in the picture; and analyzing by computation at least a pixel area corresponding to the colored print in the mold half image to determine if the colored print applied onto the mold half has any defects. Preferably, the image of the colored print applied onto a mold half can be compared with a designed image of the colored print stored in a computer as described previously. The light intensities and positions in relation to the picture center of pixels in an image of the colored print and in the designed image of the colored print can be compared as a whole, by analyzing all portions of each image in a systematic manner. More preferably, the images can be compared in discrete zones. Even more preferably, the colored print applied onto the mold half, the image of the colored print on the mold half, and the designed image of the colored print stored in a computer all are aligned at a predetermined angular orientation.

In a more preferred embodiment, the image of the mold half having the colored print on its molding surface and passing inspection is used to compare it with the image of the mold with the colored contact lens therein.

In a further aspect, the invention provides a method for making colored contact lenses. The method of the invention comprises the steps of: (1) providing a mold including a male mold half having a first molding surface and a female mold half having a second molding surface, wherein the male and female mold halves are configured to receive each other such that a mold cavity is formed between the first and second molding surfaces when the mold is closed, wherein at least one of the first and second molding surfaces is optically-transparent or translucent; (2) applying a colored print onto an area of a to-be-printed molding surface which is the first or second molding surface; (3) automatically inspecting quality of the colored print applied on the to-be-printed mold half by (a) taking a first picture, wherein the first picture comprises a first image of the mold half with the colored print applied thereon with a camera, (b) analyzing the first image to determine if there are any defects in the colored print, and (c) rejecting the mold half having defects in the colored print thereon; (4) dispensing a specific amount of a lens-forming material into one of the male and female mold halves after successfully passing automatic inspection of the step (3); (5) mating the male and female mold halves to close the mold; (6) curing the lens-forming material located between the two mold halves, thereby forming a molded colored contact lens, wherein the colored print detaches from the molding surface and becomes integral with the body of the colored contact lens; (7) separating the mold into the male and female mold halves, with the colored contact lens adhered on a lens-adhering mold half which is one of the male and female mold halves; (8) optionally and automatically inspecting the colored contact lens adhering on the lens-adhering mold half, wherein the step (8) includes taking a second picture which comprises a second image of the lens-adhering mold half with the colored contact lens thereon and comparing at least each pixel of a pixel area corresponding to the colored print in the second image with each pixel of the first image to determine if the quality of the colored print is substantially preserved during transferring of the colored print from the to-be-printed molding surface to the colored contact lens; (9) removing the colored contact lens from the lens-adhering mold half; and (10) optionally and automatically inspecting the colored contact lens removed from the lens-adhering mold half, wherein the step (10) includes taking a third picture which comprises a third image of the colored contact lens removed from the lens-adhering mold half and comparing at least each pixel of a pixel area corresponding to the colored print in the third image with each pixel of the first image and/or the second image to determine if the colored print applied onto the colored contact lens has any defects, provided that the method comprises at least one of the steps (8) and (10).

In accordance with the invention, the first picture is preferably taken with a camera which is aligned in a precisely predetermined manner with the mold having the colored contact lens therein, wherein predetermined alignment of the camera with the mold ensures that the center of the first image is located substantially at a predetermined pixel in the first picture. At least a pixel area corresponding to the colored print in the first image is analyzed by computation to determine if the colored print has any defects. Preferably, the first image is compared with a designed image of the colored print stored in a computer as described previously. More preferably, the first image and the designed image are aligned at a predetermined angular orientation.

In accordance with the invention, automatic inspection of quality of the colored print on a colored contact lens adhering on the lens-adhering mold half ensures that the quality of the colored print is substantially preserved during transferring of the colored print from the to-be-printed molding surface to the colored contact lens. With such inspection step, one can reject any colored lenses with defected colored prints applied thereon and avoid further processing of those colored lenses with defected colored prints applied thereon. Preferably, the second picture is taken with a camera which is aligned, in a precisely predetermined manner, with the lens-adhering mold half, wherein predetermined alignment of the camera with the lens-adhering mold half ensures that the center of the second image is located substantially at a predetermined pixel in the second picture. More preferably, the first and second images of the colored print are aligned at a predetermined angular orientation, preferably in a concomitant manner. With such predetermined angular orientation, it is more easily to compare the two images to check any print defects and/or to determine the rotation of the colorant layers.

In accordance with the invention, automatic inspection of the colored print of the colored contact lens removed from the lens-adhering mold half can be carried out in a lens holder containing a liquid. Any lens holders can be used in the invention. Examples of lens holders include without limitation lens inspection cells and lens packages or containers. Examples of lens inspection cells includes without limitation those described in U.S. Pat. Nos. 6,047,082, 6,776,044, 6,765,661, 6,614,516, 6,606,150, which are herein incorporated by references in their entireties. Any known suitable inspection procedures and algorithms can be used in the invention. The liquid can be water, a saline, a buffered saline, or a packaging solution known to a person skilled in the art.

In accordance with the invention, the step (10) can further comprises automatic inspection of the colored contact lenses for mechanical defects in lens materials, for foreign material attached to the lens, and for edge defects (e.g., nicks, cuts, chops and adhering foreign matter on the rim of the lens). Mechanical defects in the lens material include without limitation tears, nicks, cuts, holes, folds, and other problems. Any kind of dirt or "flash" that is attached to the lens can be a functional and safety problem, and must be detected. The edge of lenses must be smooth and continuous. Any edge defects on the rim of the contact lenses must be detected and rejected. A person skilled in the art will know well how to automatically inspect the above-described defects.

In a preferred embodiment, automatic inspection of the colored print of the colored contact lens removed from the lens-adhering mold half is carried out according to the procedures described in U.S. Pat. No. 6,047,082 (herein incorporated by reference in its entirety.

Previously-described various embodiments of colored prints, printing methods, inks, lens molds, lens-forming materials, methods for curing a lens-forming material, centering and adjusting means, cameras, taking pictures (or capturing images), and analysis of images for defects can be incorporated in this aspect of the invention.

In a still further aspect, the invention provides a method for making colored contact lenses. The method of the invention comprises the steps of: (1) providing a mold including a male mold half having a first molding surface and a female mold half having a second molding surface, wherein the male and female mold halves are configured to receive each other such that a mold cavity is formed between the first and second molding surfaces when the mold is closed, wherein at least one of the first and second molding surfaces is optically-transparent or translucent; (2) applying a colored print onto an area of a to-be-printed molding surface which is the first or second molding surface; (3) dispensing a specific amount of a lens-forming material into one of the male and female mold halves; (4) mating the male and female mold halves to close the mold; (5) optionally and automatically inspect quality of the colored print, wherein the inspection is carried out by (a) taking a first picture, wherein the first picture comprises a first image of the mold with the colored print and with the lens-forming material therein with a camera, (b) analyzing the first image to determine if there are any defects in the colored print; (6) curing the lens-forming material located between the two mold halves, thereby forming a molded colored contact lens, wherein the colored print detaches from the molding surface and becomes integral with the body of the colored contact lens; (7) optionally prior to opening the mold, automatically inspect quality of the colored print, wherein the inspection is carried out by (d) taking a second picture, wherein the second picture comprises a second image of the mold with the colored contact lens therein, (b) analyzing the second image to determine if there are any defects in the colored print, and (c) rejecting the mold containing the colored contact lens having defects in the colored print; (8) separating the mold into the male and female mold halves, with the colored contact lens adhered on a lens-adhering mold half which is one of the male and female mold halves; (9) optionally and automatically inspecting the colored contact lens adhering on the lens-adhering mold half, wherein the step (9) includes taking a third picture comprising a third image of the lens-adhering mold half with the colored contact lens thereon and comparing at least each pixel of a pixel area corresponding to the colored print in the third image with each pixel of the first or second image or both to determine if the quality of the colored print is substantially preserved during transferring of the colored print from the to-be-printed molding surface to the colored contact lens; (10) removing the colored contact lens from the lens-adhering mold half; and (11) optionally and automatically inspecting the colored contact lens from the lens-adhering mold half, wherein the step (11) includes taking a fourth picture comprising a fourth image of the colored contact lens removed from the lens-adhering mold half and comparing at least each pixel of a pixel area corresponding to the colored print in the fourth image with each pixel of the first, second, or third image or a combination thereof to determine if the colored print applied onto the colored contact lens has any defects, provided that the method comprises at least one of the steps (9) and (11) and at least one of the steps (5) and (7).

In accordance with the invention, the first or second pictures is preferably taken with a camera which is aligned, in a precisely pre-determined manner, with the mold having the colored contact lens therein, wherein predetermined alignment of the camera with the mold ensures that the center of the first image is located substantially at a predetermined pixel in the first picture. At least a pixel area corresponding to the colored print in the first or second image is analyzed by computation to determine if the colored print has any defects. Preferably, the first or second image is compared with a designed image of the colored print stored in a computer as described previously. More preferably, the first or second image and the designed image are aligned at a predetermined angular orientation.

In accordance with the invention, automatic inspection of quality of the colored print on a colored contact lens adhering on the lens-adhering mold half ensures that the quality of the colored print is substantially preserved during transferring of the colored print from the to-be-printed molding surface to the colored contact lens. With such inspection step, one can reject any colored lenses with defected colored prints applied thereon and avoid further processing of those colored lenses with defected colored prints applied thereon. Preferably, the third picture is taken with a camera which is aligned, in a precisely predetermined manner, with the lens-adhering mold half, wherein predetermined alignment of the camera with the lens-adhering mold half ensures that the center of the third image is located substantially at a predetermined pixel in the third picture. More preferably, the first, second, and third images of the colored print are aligned at a predetermined angular orientation, preferably in a concomitant manner. With such predetermined angular orientation, it is more easily to compare the two images to check any print defects and/or to determine the rotation of the colorant layers.

In accordance with the invention, automatic inspection of the colored print of the colored contact lens removed from the lens-adhering mold half can be carried out in a lens holder. Any lens holders can be used in the invention. Examples of lens holders include without limitation lens inspection cells and lens packages or containers. Examples of lens inspection cells includes without limitation those described in U.S. Pat. Nos. 6,047,082, 6,776,044, 6,765,661, 6,614,516, 6,606,150, which are herein incorporated by references in their entireties. Any known suitable inspection procedures and algorithms can be used in the invention. For example, In accordance with the invention, the step (10) can further comprises automatic inspection of the colored contact lenses for mechanical defects in lens materials, for foreign material attached to the lens, and for edge defects (e.g., nicks, cuts, chops and adhering foreign matter on the rim of the lens). Mechanical defects in the lens material include without limitation tears, nicks, cuts, holes, folds, and other problems. Any kind of dirt or "flash" that is attached to the lens can be a functional and safety problem, and must be detected. The edge of lenses must be smooth and continuous. Any edge defects on the rim of the contact lenses must be detected and rejected. A person skilled in the art will know well how to automatically inspect the above-described defects.

In a preferred embodiment, automatic inspection of the colored print of the colored contact lens removed from the lens-adhering mold half is carried out according to the procedures described in U.S. Pat. No. 6,047,082 (herein incorporated by reference in its entirety.

Previously-described various embodiments of colored prints, printing methods, inks, lens molds, lens-forming materials, methods for curing a lens-forming material, centering and adjusting means, cameras, taking pictures (or capturing images), and analysis of images for defects can be incorporated in this aspect of the invention.

The approaches to lens inspection could have different computer algorithms or inspection schemes, depending upon the manufacturing step. For example, the method to inspect the lens immediately after the printer step should focus on the print quality alone, but the method to inspect the lens after lens formation should focus on print quality and lens quality. Different inspection schemes could be done after the printing step, after lens formation, after mold separation, after lens demolding, after lens has been inserted into a package, and after lens autoclave. This could be done either automatically (in-process), semi-automatically (after process, loaded manually, but inspected with an automatic inspection system), or manually.

Alternatively, the print could be inspected in a step-wise approach. For example, the mold or lens could be imaged between print layers, to ensure that each printing step is printed correctly. This would provide the maximum print control and assurance, and good for identifying problems during development.

The invention also provides various pattern recognition methods to help separate among required elements (i.e., print pattern, inversion marks), obscuring elements (i.e., bubbles in solution, scratches on the mold or particulate in solution), and non-desired elements (i.e., nicks, scratches, bubbles in the lens). For example, these elements can be identified by using a combination of bright and darkfield analysis, but not for colored contact lenses.

Print element structures could be defined by the contact lens designer (i.e., dots, ellipses, or even reproducible irregular shapes), which could be loaded into the pattern recognition description. Any identified patterns on the contact lens that match that scheme would be identified as print, and, if desired at that location, would pass for good print quality.

Basic pattern recognition schemes separate between required, obscuring, and non-desired elements could be based upon geometric specifications, such as the circularity value. This algorithm defines each element as how close it approaches a circle (perfect circle=1, straight line=0). The good print could be defined based upon circularity value, particularly if the designer uses circular elements. Alternatively, a range of circularity values could be used to screen print quality. This scheme would be particularly good in sorting spikes, tears, nicks, lines (with low circularity values) and bubbles (with high circularity values). Other geometrical specifications could include aspect ratio, fractal number, or symmetry.

Another alternate pattern recognition scheme would be to recognize colored areas as groups. For example, individual colored elements could be recognized together as individual parts of a large group. This grouping could be done based upon colored elements of the same color, or upon multiple colored elements. This large group could be realized or quantified by a shape, density, or intensity (either black and white or color intensity) function. The sum of the groups would help define the overall colored lens image.

Various lighting schemes could be used to help identify between required, obscuring, and non-desired elements. For example, filters could be used help separate or improve the color contrast between different layers. Polarizing or cross-polarizing filter could be used to help identify anisotropic elements. Polarized, uniform, and non-uniform lighting conditions could be used to help identify the elements of interest.

The combination of bright and dark field analysis could be used to help separate among required, obscuring, and non-desired elements. Summing the light and dark field images could be used to emphasize particulate matter, which is particularly important in the optical zone.

Various photographic schemes could be used to identify required, obscuring, and non-desired elements. For example, a background image of the mold or cuvette could be taken before the lens or print is placed into the field. The subtraction of the first will eliminate any defects in the background, such as mold defects or cuvette scratches. Depending upon the background, these background defects could be used to reject lenses (i.e., mold defects), or are simply eliminated to help emphasize print quality (i.e., in the case of cuvette scratches).

Two pictures of each lens could be taken, with the lens holder rotated between images. Images processing could be used to align the print of the two images. Any difference observed are obscuring elements, such as bubbles in solution or dirt in the solution. This is a good system for inspection after lens has been demolded and is in an inspection cuvette or blister pack.

Use of top-lighting or side lighting could be used to obtain color information from the print. Each pixel element would have an associated RGB value. Each color layer could be compared with a reference value or range, or with an ideal image. This could help identify which image layer is printing poorly. This system could possibly determine if the ink color is within a certain color range as a QA check.

Previous inspection system has much emphasis on ensuring the print center is aligned with the lens center. Not all print patterns require this scheme; the relationship of each print layer with respect to subsequent layers may be developed with any need for alignment or measurement, as long as they are printed within the lens. Alternatively, one layer only has to fit within a previous layer to achieve good print; the previous print layer would be able to obscure any variance in the subsequent print (i.e., the outer starburst is able to obscure any variance in the iris pattern within about 200 microns). For example, the inspection scheme would only have to identify print the first layer outside or inside of the second layer to fail print quality.

Another aspect of the invention is determining the centralization of the print relative to the edge of the lens. Prior art does this by first finding the center of the lens. This has a disadvantage in that the consumer judges the centralization of the print when wearing the lens by judging distance of the print to the outer edge of the lens. The center of the lens is not as easy to be discerned by to the customer. This aspect of the invention is a method to evaluate centralization of the printed pattern by having the automatic inspection system evaluate the adequacy of pattern centralization be measuring the difference in distance between the edge of the lens and the edge of the pattern. This measurement is compared to the same difference at a point opposite the first measurement. The differences are subtracted and the subtracted value must be less than a specified value. This technique can be used for one or all of the patterns on a lens.

Alternatively, the captured image can be compared with a reference location on the lens which is not central with respect to the contact lens or print center. While this off-center reference mark could be used for spherical lenses, this is preferentially used for toric lenses. Toric lenses would require a reference mark to identify the toric, horizontal angle, and/or rotation mark, and determine if rest of image oriented to the toric angle mark. Optionally, an off-axes reference mark would be beneficial for ballasted products, such as Wild-Eyes (Cat-Eye), or lenses for presbyopia. This reference mark may not necessarily be printed; reference marks for ballasted lenses or lenses for astigmatism could be accomplished by measuring power of lens thickness, either on-line or off-line. Scribe marks could be used as well.

The previous disclosure will enable one having ordinary skill in the art to practice the invention. Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A method for making colored contact lenses, comprising the steps of:
   (1) providing a mold comprising a male mold half having a first molding surface and a female mold half having a second molding surface, wherein the male and female mold halves are configured to receive each other such that a mold cavity is formed between the first and second molding surfaces when the mold is closed, wherein at least one of the first and a second molding surfaces is optically-transparent or translucent;
   (2) applying a colored print onto an area of a to-be-printed molding surface wherein the to-be-printed molding surface is selected from the first and second molding surfaces;
   (3) automatically inspecting the colored print applied on the printed mold half by (a) capturing a first picture, wherein the first picture comprises a first image of the mold half with the colored print applied thereon with a camera, (b) analyzing the first image to determine if there are any defects in the colored print and (c) rejecting the mold half having defects in the colored print thereon, wherein the first picture is taken with a camera which is aligned, in a precisely predetermined manner, with the mold half having the colored print thereon, wherein predetermined alignment of the camera with the mold half ensures that the center of the first image of the mold is located substantially at a predetermined pixel in the first picture;
   (4) dispensing a specific amount of a lens-forming material into one of the male and female mold halves after successfully passing automatic inspection of the step (3);
   (5) mating the male and female mold halves to close the mold;
   (6) curing the lens-forming material located between the two mold halves, thereby forming a molded colored contact lens, wherein the colored print detaches from the molding surface and becomes integral with the body of the colored contact lens;
   (7) separating the mold into the male and female mold halves, wherein the colored contact lens adheres to one of the male and female mold halves; and
   (8) removing the colored contact lens from the lens-adhering mold half.

2. The method of claim 1, wherein at least a pixel area corresponding to the colored print in the first image is analyzed by computation to determine if the colored print has any defects.

3. The method of claim 1, wherein the first image is compared with a designed image of the colored print stored in a computer, as a whole or in discrete zones.

4. The method of claim 3, wherein the first image and the designed image are aligned at a predetermined angular orientation.

5. The method of claim 1, wherein after step (7) further comprising automatic inspection of the colored contact lenses for mechanical defects in lens materials, for foreign material attached to the lens, and for edge defects.

6. A method for making colored contact lenses, the method comprising the steps of:
   (1) providing a mold including a male mold half having a first molding surface and a female mold half having a second molding surface, wherein the male and female mold halves are configured to receive each other such that a mold cavity is formed between the first and second molding surfaces when the mold is closed, wherein at least one of the first and second molding surfaces is optically-transparent or translucent;
   (2) applying a colored print onto an area of a to-be-printed molding surface which is the first or second molding surface;
   (3) dispensing a specific amount of a lens-forming material into one of the male and female mold halves;
   (4) mating the male and female mold halves to close the mold;
   (5) curing the lens-forming material located between the two mold halves, thereby forming a molded colored contact lens, wherein the colored print detaches from the molding surface and becomes integral with the body of the colored contact lens;
   (6) prior to opening the mold, automatically inspecting quality of the colored print, wherein the inspection is carried out by (a) capturing a first picture, wherein the first picture comprises a first image of the mold with the colored contact lens therein, (b) analyzing the first image to the determined if there are any defect in the colored, and (c) rejecting the mold containing the colored contact lens having defects in the colored print wherein the first picture is taken with a camera which is aligned, in a precisely predetermined manner, with the mold having the colored contact lens therein, wherein predetermined alignment of the camera with the mold ensures that the center of the first image of the mold is located substantially at a predetermined pixel in the first picture;
   (7) separating the mold, which passes the inspection of the step (6), into the male and female mold halves, with the colored contact lens adhered on a lens-adhering mold half which is one of the male and female mold halves; and
   (8) removing the colored contact lens from the lens-adhering mold half.

7. The method of claim 6, wherein after step (7), further comprising automatically inspecting the colored contact lens adhering on the lens-adhering mold half by (a) capturing a second picture comprising a second image of the lens-adhering mold half with the colored contact lens thereon and comparing at least each pixel of a pixel area corresponding to the colored print in the second image with each pixel of the first image to determine if the quality of the colored print is substantially preserved transferring of the colored print from the printed molding surface to the colored contact lens.

8. The method of claim 6, wherein the first image is compared with a designed image of the colored print stored in a computer, as a whole or in discrete zones.

9. The method of claim 6, wherein the first image and the designed image are aligned at a predetermined angular orientation.

10. The method of claim 6, further comprising automatic inspection of the colored contact lenses for mechanical defects in lens materials, for foreign material attached to the lens, and for edge defects.

11. A method for automatically inspecting a colored print applied on a mold half, comprising the steps of:
  (1) obtaining a mold half including a molding surface, wherein the molding surface includes a colored print;
  (2) automatically aligning, in a precisely predetermined manner, by using centering and adjusting means, a camera with the mold half having the colored print on its molding surface;
  (3) taking a picture with the camera, wherein the picture comprises an image of the mold half having the colored print on its molding surface, wherein predetermined alignment of the camera with the mold half ensures that the center of the mold half image is located substantially at a predetermined pixel in the picture; and
  (4) analyzing by computation at least a pixel area corresponding to the colored print in the mold half image to determine if the colored print applied onto the mold half has any defects.

12. The method of claim 11, wherein the image is compared with a designed image of the colored print stored in a computer, as a whole or in discrete zones.

13. The method of claim 12, wherein the image and the designed image are aligned at a predetermined angular orientation.

14. A method for automatically inspecting a colored print applied on a contact lens which is cast-molded in a mold having a male half and female mold half, each mold half have a molding surface, the method comprising the steps of:
  (1) curing a lens-forming material in a mold for making a contact lens to form a colored contact lens, wherein the mold comprises a male mold half with a first molding surface and a female mold half having a second molding surface, wherein the male and female mold halves are configured to receive each other such that a mold cavity is formed between the first and second molding surfaces when the mold is closed, wherein at least one of the first and second molding surface has a colored print applied thereon prior to dispensing the lens-forming material in the cavity, wherein at least one of the first and second molding surfaces is optically transparent or translucent, wherein the colored print detaches from the molding surface and becomes integral with the body of the colored contact lens; and
  (2) prior to opening the mold, automatically inspecting colored print quality, wherein this step includes
    (a) automatically aligning, in a precisely predetermined manner and by using centering and adjusting means, a camera with the mold with the colored contact lens therein, wherein the camera is facing one of the mold halves having the optically-transparent or translucent molding surface,
    (b) taking a first picture with the camera, wherein the first picture comprises a first image of the mold with the colored contact lens therein, wherein predetermined alignment of the camera with the mold ensures that the center of the first image is located substantially at a predetermined pixel in the first picture, and
    (c) analyzing at least a pixel area corresponding to the colored print in the first image to determine if the colored print applied onto the colored contact lens has any defects.

15. The method of claim 14, wherein the first image is compared with a designed image of the colored print stored in a computer, as a whole or in discrete zones.

16. The method of claim 15, wherein the first image and the designed image are aligned at a predetermined angular orientation.

17. The method of claim 14, further comprising, before the step (1), the steps of: (a) applying the colored print applied onto at least one of the first and second molding surface prior to dispensing the lens-forming material in the cavity; (b) automatically aligning, in a precisely predetermined manner and by using centering and adjusting means, a camera with the mold half having the colored print on its molding surface; (c) taking a second picture with the camera, wherein the second picture comprises a second image of the mold half having the colored print on its molding surface, wherein predetermined alignment of the camera with the mold half ensures that the center of the second image is located substantially at a predetermined pixel in the second picture; and (d) analyzing by computation at least a pixel area corresponding to the colored print in the second image to determine if the colored print applied onto the mold half has any defects.

18. The method of claim 17, wherein the second image is compared with a designed image of the colored print stored in a computer, as a whole or in discrete zones.

19. The method of claim 18, wherein the second image and the designed image are aligned at a predetermined angular orientation.

20. The method of claim 17, wherein the second image is compared with the first image to determine if the quality of the colored print is substantially preserved during transferring of the colored print from the to-be-printed molding surface to the colored contact lens.

* * * * *